United States Patent
Gabriel, Sr. et al.

(10) Patent No.: US 9,192,479 B2
(45) Date of Patent: Nov. 24, 2015

(54) SPACERS FOR REDISTRIBUTING FORCES FOR THE PATELLA

(71) Applicant: Moximed, Inc., Hayward, CA (US)

(72) Inventors: Stefan Gabriel, Sr., Mattapoisett, MA (US); Anton G. Clifford, Mountain View, CA (US); Joshua Makower, Los Altos, CA (US); David Lowe, Redwood City, CA (US); Michael E. Landry, Austin, TX (US); Heber Saravia, San Francisco, CA (US); Josef L. Friedmann, Scotts Valley, CA (US)

(73) Assignee: MOXIMED, INC., Hayward, CA (US)

( * ) Notice: Subject to any disclaimer, the term of this patent is extended or adjusted under 35 U.S.C. 154(b) by 87 days.

(21) Appl. No.: 13/708,504

(22) Filed: Dec. 7, 2012

(65) Prior Publication Data
US 2013/0150977 A1    Jun. 13, 2013

Related U.S. Application Data

(60) Provisional application No. 61/568,615, filed on Dec. 8, 2011.

(51) Int. Cl.
*A61F 2/38* (2006.01)
*A61B 17/56* (2006.01)

(52) U.S. Cl.
CPC ............... *A61F 2/3859* (2013.01); *A61B 17/56* (2013.01); *A61B 2017/564* (2013.01); *A61B 2017/568* (2013.01); *A61F 2/3877* (2013.01)

(58) Field of Classification Search
CPC A61F 2/38; A61F 2/3877; A61F 2002/30892
USPC ............................................. 623/20.14–20.21
See application file for complete search history.

(56) References Cited

U.S. PATENT DOCUMENTS

| | | | |
|---|---|---|---|
| 4,052,753 A | 10/1977 | Dedo | |
| 2010/0131069 A1* | 5/2010 | Halbrecht | 623/20.2 |
| 2010/0198354 A1 | 8/2010 | Halbrecht | |
| 2011/0213466 A1 | 9/2011 | Shenoy et al. | |

FOREIGN PATENT DOCUMENTS

EP    1 410 769    4/2004

OTHER PUBLICATIONS

Communication Relating to the Results of the Partial International Search in corresponding International Application No. PCT/US2012/068553 mailed on Feb. 19, 2013.
International Search report and Written Opinion of the International Searching Authority mailed Apr. 24, 2013 in corresponding International Application No. PCT/US2012/068553.

* cited by examiner

Primary Examiner — Jason-Dennis Stewart
(74) Attorney, Agent, or Firm — Adam J. Cermak; Cermak Nakajima & McGowan LLP

(57) ABSTRACT

Implant apparatus and methods directed toward treating conditions involving the knee joint and the patella specifically are disclosed. Full range of motion of the knee joint and tissue integrity are maintained in treatment approaches involving implanting a joint surface load reducing implant proximate the joint to change the direction of the tendons or muscles exerting forces on the joints.

18 Claims, 17 Drawing Sheets

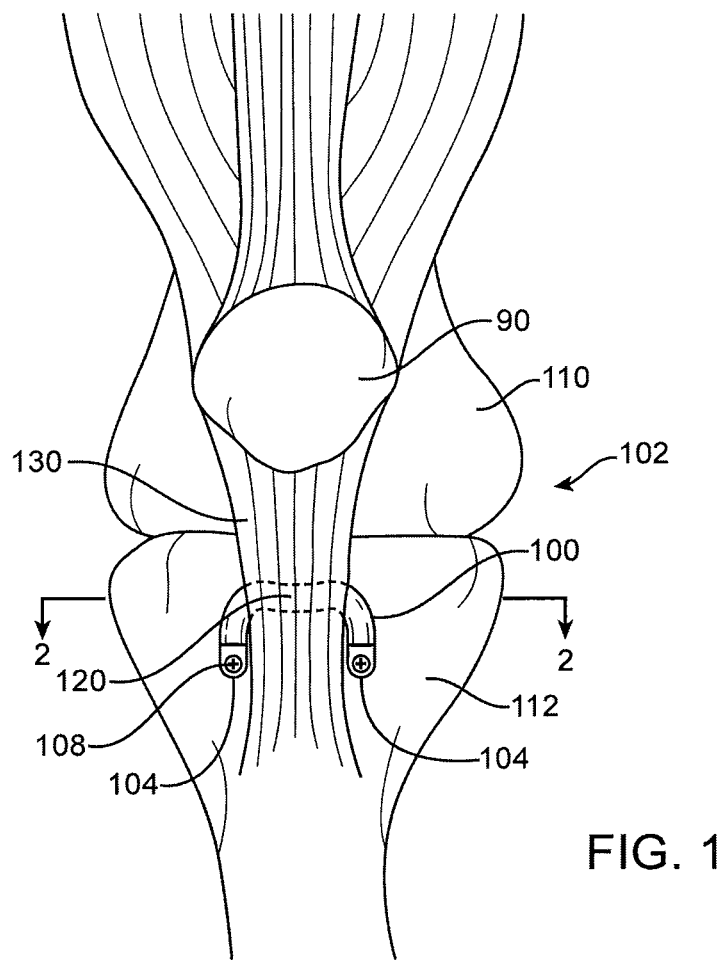
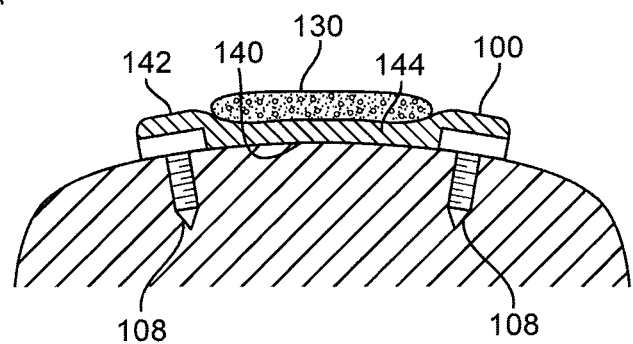
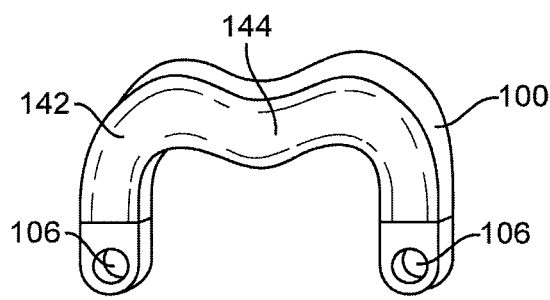
FIG. 1
FIG. 2
FIG. 3

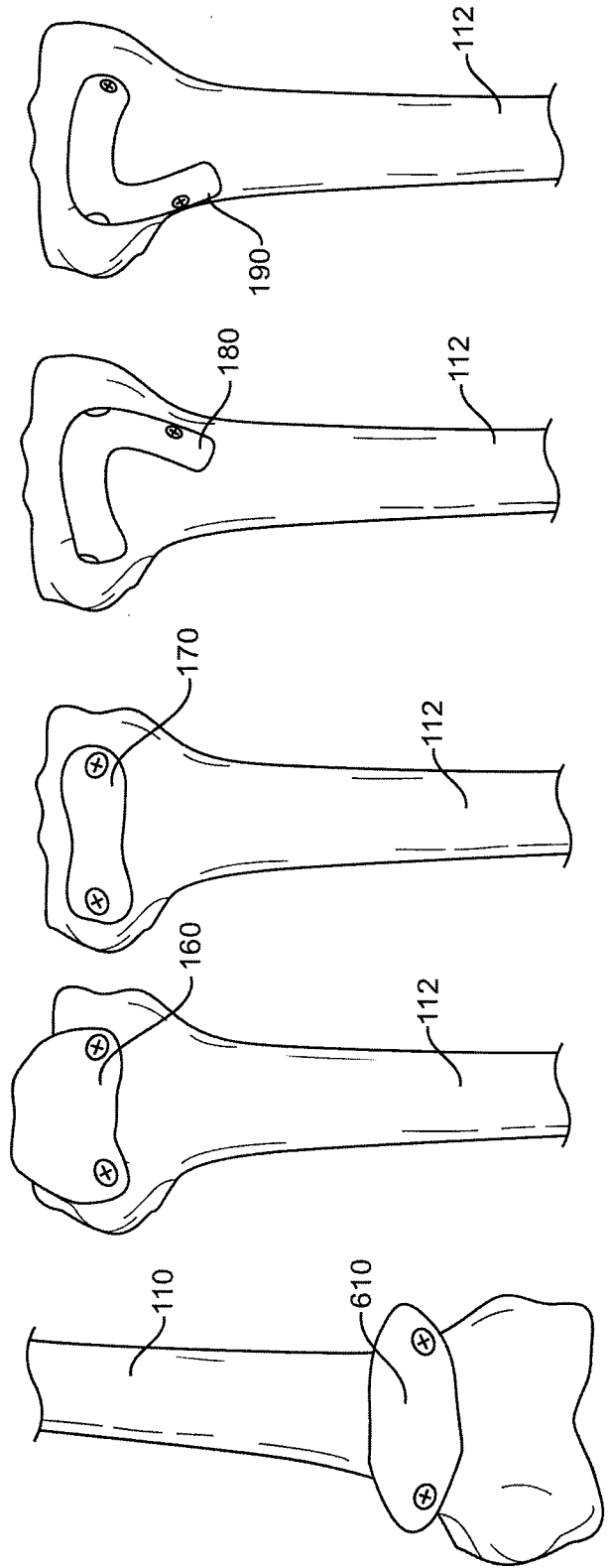

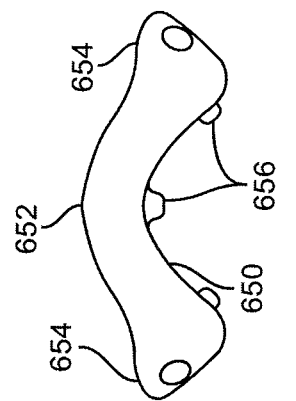
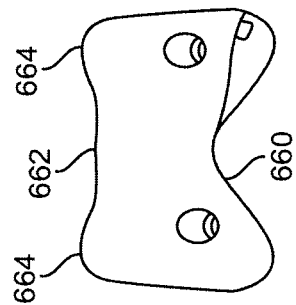
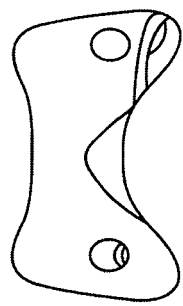
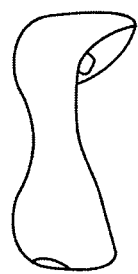

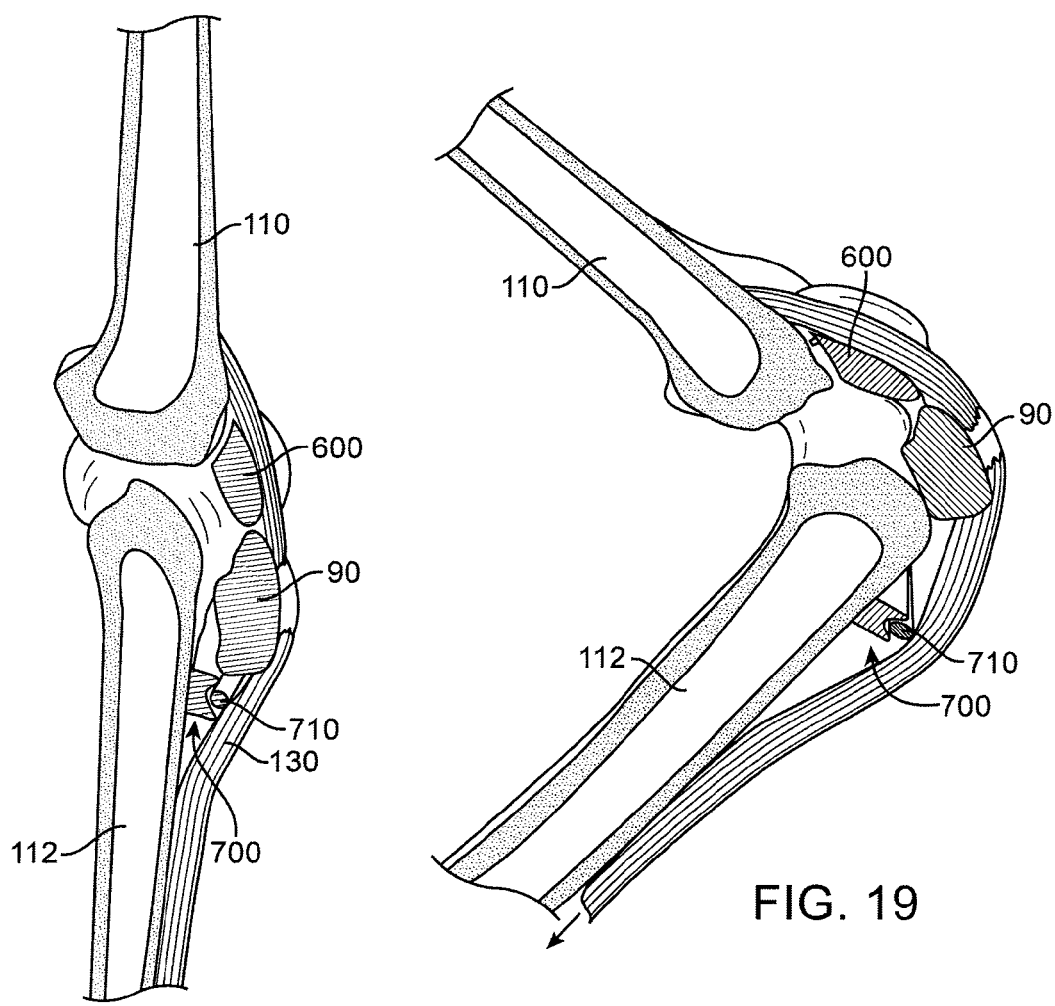
FIG. 18
FIG. 19
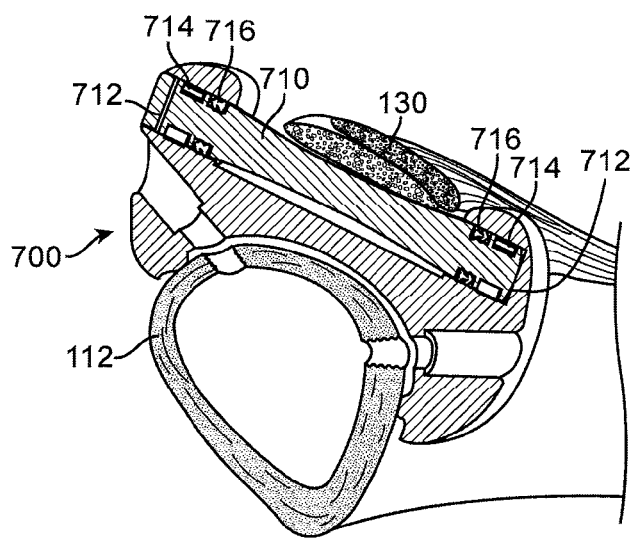
FIG. 20

SPACERS FOR REDISTRIBUTING FORCES FOR THE PATELLA

CROSS-REFERENCE TO RELATED APPLICATION(S)

This application claims the benefit of U.S. Provisional Application No. 61/568,615 filed Dec. 8, 2011, which is entirely incorporated herein by reference.

BACKGROUND OF THE DISCLOSURE

The present disclosure is directed towards systems and methods for treating tissue of a body and more particularly, towards approaches designed to treat a natural joint and conditions involving the patella specifically.

A joint is the location at which two or more bones make contact. They are constructed to allow movement and provide mechanical support, and are classified structurally and functionally. Structural classification is determined by how the bones connected to each other, while functional classification is determined by the degree of movement between the articulating bones. In practice, there is significant overlap between the two types of classifications.

There are three structural classifications of joints, namely fibrous or immovable joints, cartilaginous joints and synovial joints. Fibrous/Immovable bones are connected by dense connective tissue, consisting mainly of collagen. The fibrous joints are further divided into three types: sutures which are found between bones of the skull; syndesmosis which are found between long bones of the body; and gomphosis which is a joint between the root of a tooth and the sockets in the maxilla or mandible.

Cartilaginous bones are connected entirely by cartilage (also known as "synchondroses"). Cartilaginous joints allow more movement between bones than a fibrous joint but less than the highly mobile synovial joint. Synovial joints have a space between the articulating bones for synovial fluid. This classification contains joints that are the most mobile of the three, and includes the knee and shoulder. These are further classified into ball and socket joints, condyloid joints, saddle joints, hinge joints, pivot joints, and gliding joints.

Joints can also be classified functionally, by the degree of mobility they allow. Synarthrosis joints permit little or no mobility. They can be categorized by how the two bones are joined together. That is, synchrondoses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Finally, diarthrosis joints permit a variety of movements (e.g. flexion, adduction, and pronation). Only synovial joints are diarthrodial and they can be divided into six classes: 1. ball and socket—such as the shoulder or the hip and femur; 2. Hinge—such as the elbow; 3. Pivot—such as the radius and ulna; 4. condyloidal (or ellipsoidal)—such as the wrist between radius and carps, or knee; 5. Saddle—such as the joint between carpal thumbs and metacarpals; and 6. Gliding—such as between the carpals.

Synovial joints (or diarthroses, or diarthroidal joints) are the most common and most movable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibro-cartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Maladies that can affect the knee joint specifically include patellar or kneecap pain, misalignment or dislocation. Pain can exist when there is an excess of force contact between the patella and femur. This can be due to misalignment associated arthritis or anatomical conditions specific to an individual. Kneecap dislocation occurs when the triangle-shaped patellar bone covering the knee moves or slides out of place. This problem usually occurs toward the outside of the leg and can be the result of patella misalignment due to patient specific anatomy or osteoarthritis, or from trauma.

The patella rests in the patellofemoral groove, a cavity located on the knee between the distal femur and the tibia. The sides of the patella attach to certain ligaments and tendons to stabilize and support it. The upper border of the patella attaches to the common tendon of the quadriceps muscles. The side or medial borders of the patella are attached to the vastus medialis muscle, and the lower border of the patella is connected by the patellar ligament to the tibial tuberosity. The main ligament stabilizer, the patellofemoral ligament, rests directly over the femur and the patella while the lateral and medial collateral ligaments acts as the secondary ligament stabilizers from either side of the patella.

Arthritis of the patella is one of the many causes of knee pain. Patella femoral arthritis, is identified when loss of cartilage behind the patella leads to pain in the knee. The pain typically worsens when a patient walks hills, goes up or down stairs, or does deep knee flexion. Arthritis of the patella can result from an injury to the knee joint, ordinary wear and tear, or most commonly the improper tracking of the patella on the femur when the patella does not line up properly.

Non-surgical treatments for patella femoral arthritis include exercises, anti-inflammatory drugs, weight loss, pain medication and cortisone shots to help lessen the pain. External braces or taping to improve patella tracking can also be used. However, if sufficient bone loss occurs, surgery may be necessary.

Surgical options include cartilage shaving, cartilage excision, drilling into subchondral bone to induce regeneration or a lateral release where a tendon is cut to help align the knee. Other surgical options include a tibial tuberosity osteotomy, partial knee replacement and a total knee replacement, or removal of the patella entirely.

In a tibia tuberosity osteotomy, the bump on which your patellar tendon attaches (tibial tuberosity) is moved surgically by cutting the bone and adding plates and/or pins. The tibial tuberosity is moved up, down, left or right depending on the location of the damaged cartilage to move the load on the cartilage to a part of the knee that is still healthy—assuming there is such an area.

In a patellectomy the patella is removed outright. Sometimes this works, but sometimes removing the patella may hasten the onset of arthritis in the rest of the knee. A patella replacement may also be performed where part or all of the patella is replaced with an implant.

Recently, less conventional approaches to treating the patella have been proposed. In one approach, a patellar implant is placed below a patellar tendon to elevate or tilt the patellar tendon. This consequently may alter patellar tracking and decrease forces on the patella to thereby alleviate pain caused by the patella contacting the femur or tibia or by decreasing force loads across the patella-femoral joint.

In a related approach, improper force distributions associated with the patella are addressed by displacing tissues in order to realign force vectors and alter movement across loading the knee joint. Here, again, an objective is to lessen the force with which the patella is pressed against the femur during the gait cycle.

Sufficient attention does not appear to have been given in prior patella treatment approaches, however, to treatment of the knee joint throughout its full range of motion. There is also a need for avoiding negative remodeling of the patellar ligament as well as approaches to maintain a desired alignment of an implant and target tissue.

Therefore, what is needed and heretofore lacking in prior attempts to treat joint pain associated with patella misalignment or dislocation is an implantation method and implant device which addresses full range of joint movement, and which maintains desired structural integrity of anatomy forming the knee joint.

The present disclosure addresses these and other needs.

SUMMARY

Briefly and in general terms, the present disclosure is directed towards treating joint structures. In one aspect, there are disclosed approaches to redistributing forces of the patella to alleviate pain or to address misalignment.

In one particular embodiment, there is provided an implant which is contoured to receive the patellar tendon. The contour of the implant is configured to define structure preventing the patellar tendon from disengaging from the implant during a full range of motion of a knee joint. The implant is also contoured to avoid negative remodeling of the tissue of the knee.

In one embodiment, an implant for decreasing pain caused by misalignment of bones at a joint includes an implant body configured to be implanted beneath a tendon. The implant has a smooth upper surface for allowing a tendon to slide over the implant body during articulation of the joint and a hook shaped portion configured to receive at least a portion of the tendon within an overhang of the hook to alter the tracking of the bones of the joint and alleviate pain associated with misalignment of the bones of the joint.

In one embodiment of a method for treating a knee joint suffering from pain, the method includes the steps of inserting an implant below a patellar tendon; and configuring the implant so that it engages the patellar tendon throughout a full range of motion of the knee joint and so as to cause tension redistribution and contact force manipulation to alleviate pain.

In another embodiment of a method for treating a knee joint suffering from pain, the method includes the steps of inserting an implant below a quadriceps muscle or quadriceps tendon; fixing the implant to the femur; configuring the implant so that it engages the quadriceps muscle or quadriceps tendon throughout a range of motion of the knee joint; and reducing compressive loads between the patella and femur with the implant.

In another embodiment of a method for decreasing a force applied between two bones of a joint, the method includes the steps of affixing an implant to a tendon at a location between the tendon and a bone at a location proximate a the joint; allowing movement of the tendon and implant over the bone during articulation of the joint; and decreasing compressive loads between the two bones of the joint with the implant.

The implant can embody a fluid filled bladder which self-contours to tissues. In one aspect, the implant can be adjustable through the movement, addition or removal of fluid. Various embodiments are contemplated to treat patellar misalignment and to inhibit dislocation, as well as to absorb loads applied by the patella upon adjacent anatomy.

In a specific approach, an implant can include a two stage bladder having a main chamber for positioning under a ligament and a secondary chamber in communication with the main chamber. A valve can further be provided between the main and secondary chambers. During gait, fluid remains in the main chamber and performs ligament tensioning. During rest periods and when the limb is straight, fluid passes to the secondary chamber relieving tension on the ligament. This prevents negative remodeling or stretching of the ligament, as the same causes such therapy to become less effective over time.

An implant can include a chamber that is fluid or gas filled to provide a compliant bolster and lengthening effect to increase a moment arm of the bolstered tendon or muscle. The chamber and bladder can be inflated or expanded over time to provide an increasing size or stiffness structure, or deflated or contracted to provide an opposite effect. A valve or injection port can be utilized for this functionality.

The implant can further be configured such that when a leg is in extension, there is no force or little force in a first chamber of the implant. An elasticity of a second chamber is selected to cause fluid to flow into the first chamber. During gait, a valve between the chambers retains fluid within the first chamber. When at rest, with the joint in flexion the patella tendon presses fluid from the first chamber into the second chamber.

In yet another approach, an implant is provided to treat a joint and functions to redistribute forces of a patella. The implant includes structure accomplishing attachment of the implant to the patella tendon. This implant can be a single spacer or can include one or more chambers that contain fluid or gas. Such an implant thus remains in place during a full range of motion of a knee joint.

Other features and advantages of the present disclosure will become apparent from the following detailed description, taken in conjunction with the accompanying drawings, which illustrate, by way of example, the principles of the disclosure.

BRIEF DESCRIPTION OF THE DRAWINGS

FIG. 1 is a front view, depicting an implant attached to members defining a joint according to an embodiment of the present disclosure;

FIG. 2 is a cross-sectional view, depicting the structure of FIG. 1 taken along line 2-2;

FIG. 3 is a perspective view, depicting the implant of FIG. 1;

FIGS. 8A-8E are front views, depicting implants having different shapes attached to a bone of a joint according to an alternative example embodiments of the present disclosure;

FIGS. 9A-9D are top views of implants having different shapes according to alternative embodiments of the present disclosure;

FIG. 18 is a side cross-sectional view of the implant of FIG. 17 with the knee joint at full extension;

FIG. 19 is a side cross-sectional view of the implant of FIG. 17 with the knee joint in flexion;

FIG. 20 is cross-sectional view of the implant of FIG. 17 taken along an axis of the roller;

DETAILED DESCRIPTION OF THE PREFERRED EMBODIMENTS

Figure 4A:
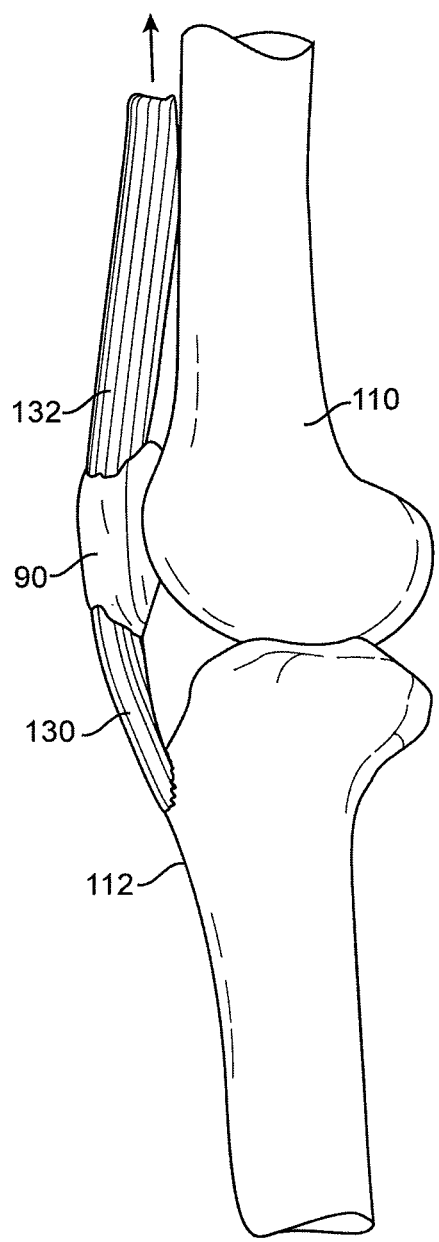
FIGS. 4A and 4B are side views, depicting a knee joint with and without tibial and femur implants.

Referring now to the drawings, which are provided by way of example and not limitation, the present disclosure is directed towards apparatus and methods for treating a joint, and in particular, for treating a knee joint and for relieving pain caused by conditions involving the patella. Patella femoral osteoarthritis can be due to natural anatomy misalignment or can be a function of an earlier injury. Significant pain can be associated with these patellar conditions and can be a direct result of excessive forces being generated between the patella and adjacent anatomy. In particular, pain results when there are undesirable force contacts between the patella and the femur. The present disclosure is directed at alleviating pain by redirecting or absorbing excess forces without permanently remodeling tissues critical to the functioning of the knee joint.

As shown in FIGS. 1-3, one approach to treating conditions involving a patella 90 can include the placement of an implant 100 at the knee joint 102. The implant 100 can be generally U-shaped and can include terminal ends 104 configured to be affixed to body anatomy. In one approach, the terminal ends 104 include through holes 106 sized and shaped to receive bone screws 108 or other affixation structure. In this way, the implant 100 can be attached directly to tibia 112 of the knee joint 102. Although the implant 100 is shown attached to the tibia 112, it can also be affixed to the femur 110 as will be discussed further below.

Although the present apparatus and method are described particularly for reducing pain of patellar chondromalacia or osteoarthritis due to damaged cartilage on the surfaces of the patella and the trochlear groove of the femur, embodiments of the disclosure can be used to relieve the loads on other joints in a similar manner. By changing the direction and position of tendons and muscles that exert forces on joints, the implants function as a tissue elevator to reduce compressive loads on joint surfaces.

As shown in FIG. 1, the implant 100 is affixed to the tibia 112 such that a midsection 120 of the implant 100 is configured under the patellar tendon 130. The terminal ends 104 of the implant 100 are shown directed away from the knee joint 102 but can alternatively be pointing toward the knee joint 102 or wrapping around the tibia 112.

The implant 100 is further contoured to define a low profile attachment structure. It is thus contemplated that a lower surface 140 of the implant 100 be curved to mimic the shape of the structure to which the implant engages, such as the tibia 112, or femur 110. An upper surface 142 is also contoured so as to fit nicely with the knee anatomy and may include a lubricious coating or material permitting relative motion between the implant and knee anatomy. The implant 100 may be provided in different sizes having different heights of the midsection 120 to allow a selection of different patellar tendon force reduction heights.

Once an implant 100 of a selected height is inserted beneath the patellar tendon 130 the effective angle of action of the patellar tendon on the patella 90 is modified reducing the force with which the patellar tendon presses the patella against the femur.

The upper surface 142 of the implant 100, as shown in FIG. 2, further includes a recess 144 designed to receive the patellar tendon 130. The recess 144 defines a trough through which the patella tendon 130 can be translated throughout a full range of articulation and valgus and varus motion or other rotation or movement of the knee joint. Thus, a portion of the patellar tendon 130 remains within the recess 144 throughout gait as well as when the knee joint 102 is in complete flexion or extension, and all angles therebetween, and when the knee joint is loaded and unloaded. Without the recess 144 or other structure for guiding the tendon over the implant 100, the tendon can slide off of the implant during a portion of the motion of the joint. In addition to guiding the tendon 130 over the implant 100 in the ordinary natural path of the tendon, the implant may also be arranged to alter the path of the tendon and thereby correct improper tracking of the patella over the femur. For example, where the patella 90 is shifted medially and this shift is causing wear and associated pain in the joint, the implant 100 can shift the patellar tendon laterally to reorient the tracking of the patella while also reducing the load on the patella by changing the angle of action of the patellar tendon. In the case of redirecting the trajectory of the patellar tendon, the recess 144 in the implant 100 can be modified to have more pronounced edges to achieve this redirection.

Figure 4B:
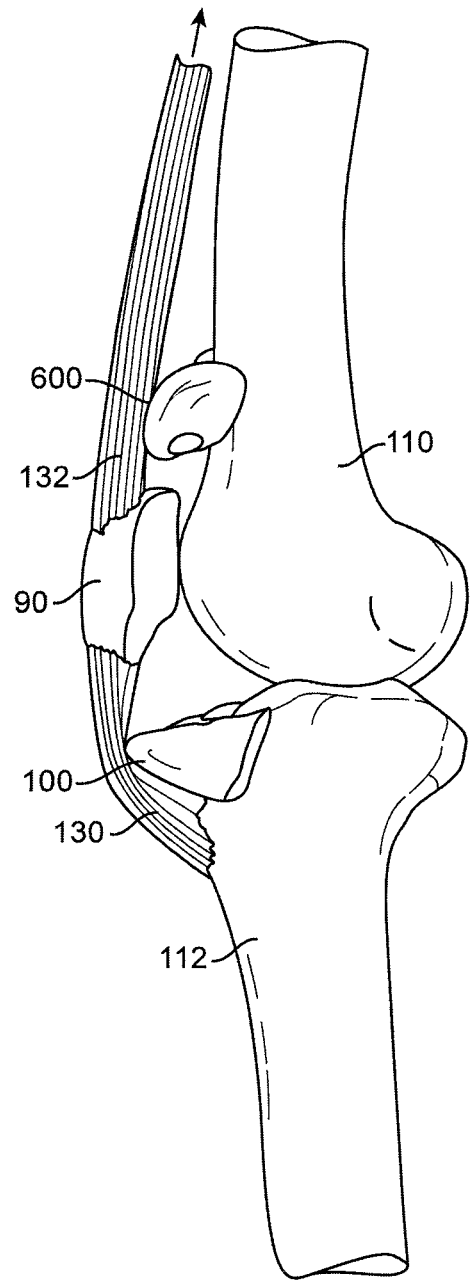

FIGS. 4A and 4B illustrate a joint at extension with and without a tibial implant 100 and a femoral implant 600 secured to the tibia and femur with bone screws (not shown). The position of the tibial implant 100 beneath the patellar tendon 130 and the femoral implant 600 beneath the quadriceps muscle or quadriceps tendon 132 reduces the load on the patellar/femoral surfaces, thus reducing patellar/femoral pain. The reduction in contact between the patellar and femoral joint surfaces can be seen by comparison of FIG. 4A without implants to FIG. 4B with implants. The magnitude of reduction in contact is dependent on the implant height selected. A large implant height is shown in FIG. 4B by way of example to more clearly show the reduction in contact forces. The patella 90 need not be lifted entirely off the patella when the knee is at full extension to provide pain relief.

Figures 5A, 5B:
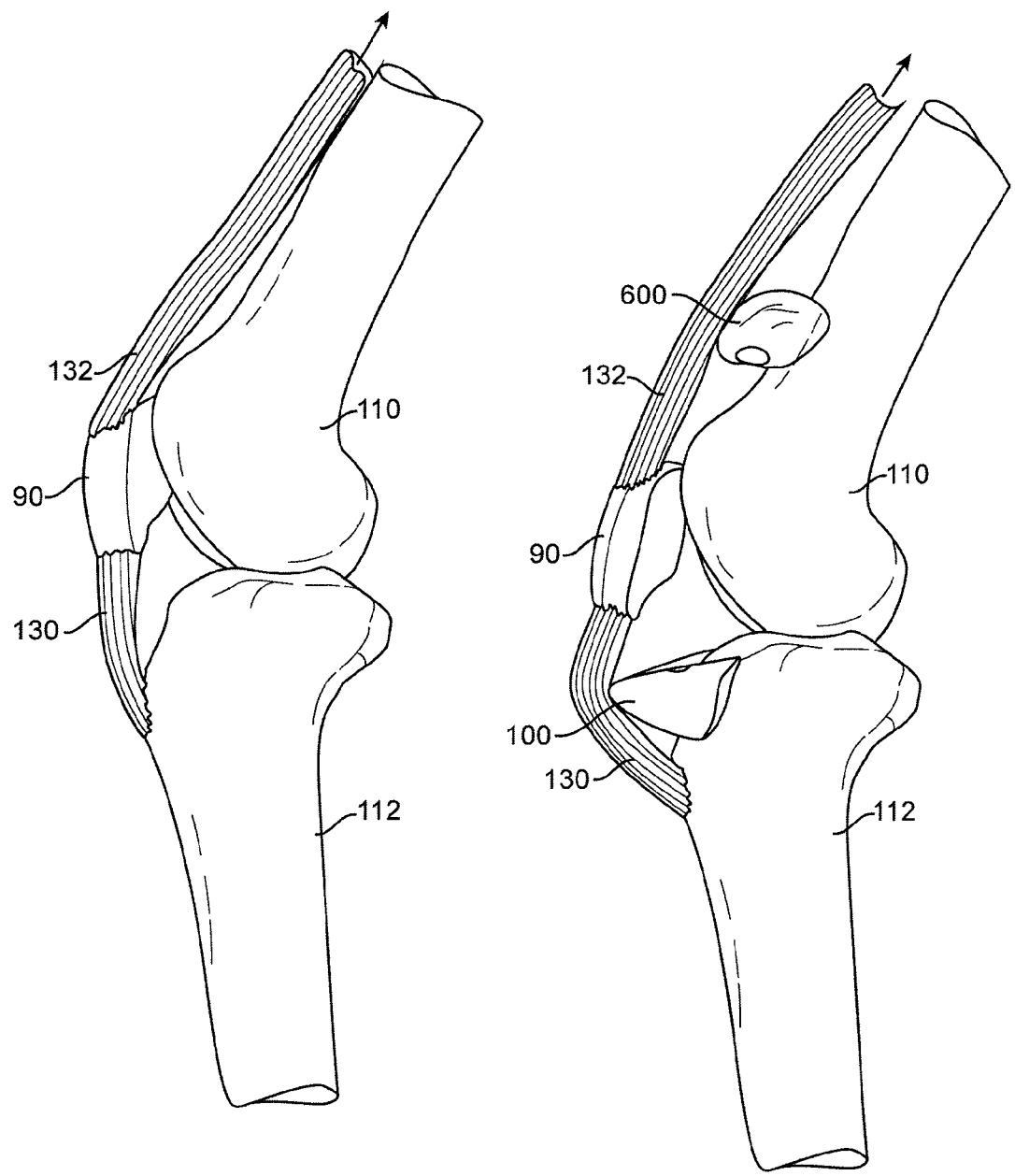
FIGS. 5A and 5B are side views, depicting the knee joint and implants of FIGS. 4A and 4B with the joint flexed to about 30 degrees.

FIGS. 5A and 5B illustrate the reduction in load between the patella 90 and the femur 110 at about 30 degrees of flexion of the joint. As can be seen in FIG. 5B, the distal portion of the patella 90 is lifted away from the femur 110, significantly reducing load at this portion of the joint at partial flexion.

Figure 6A:
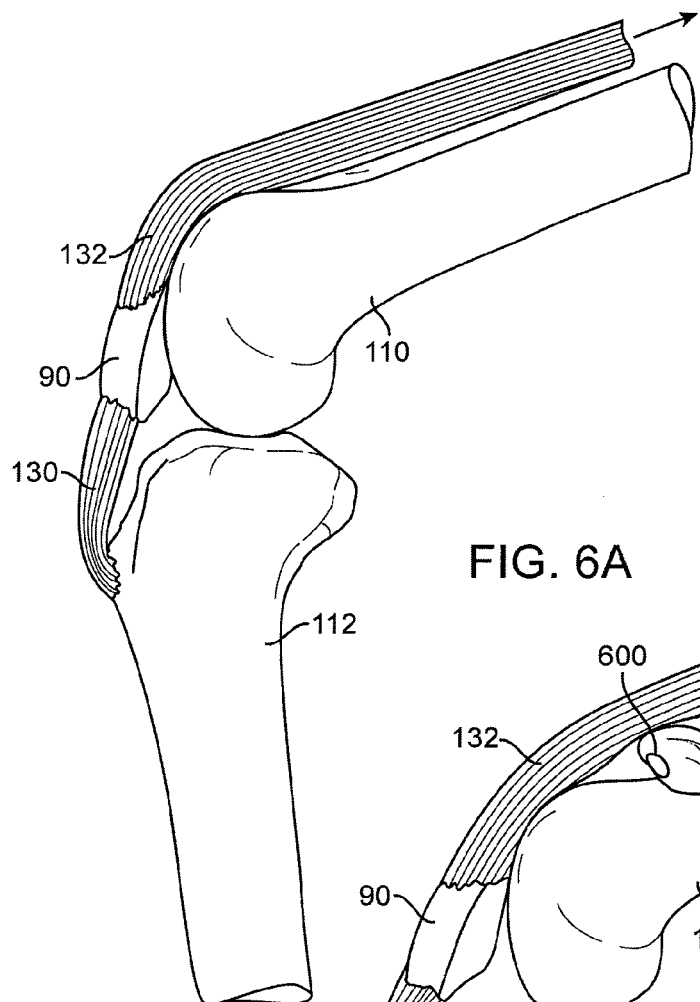
FIGS. 6A and 6B are side views, depicting the knee joint and implants of FIGS. 4A and 4B with the joint flexed to about 75 degrees.
Figure 6B:
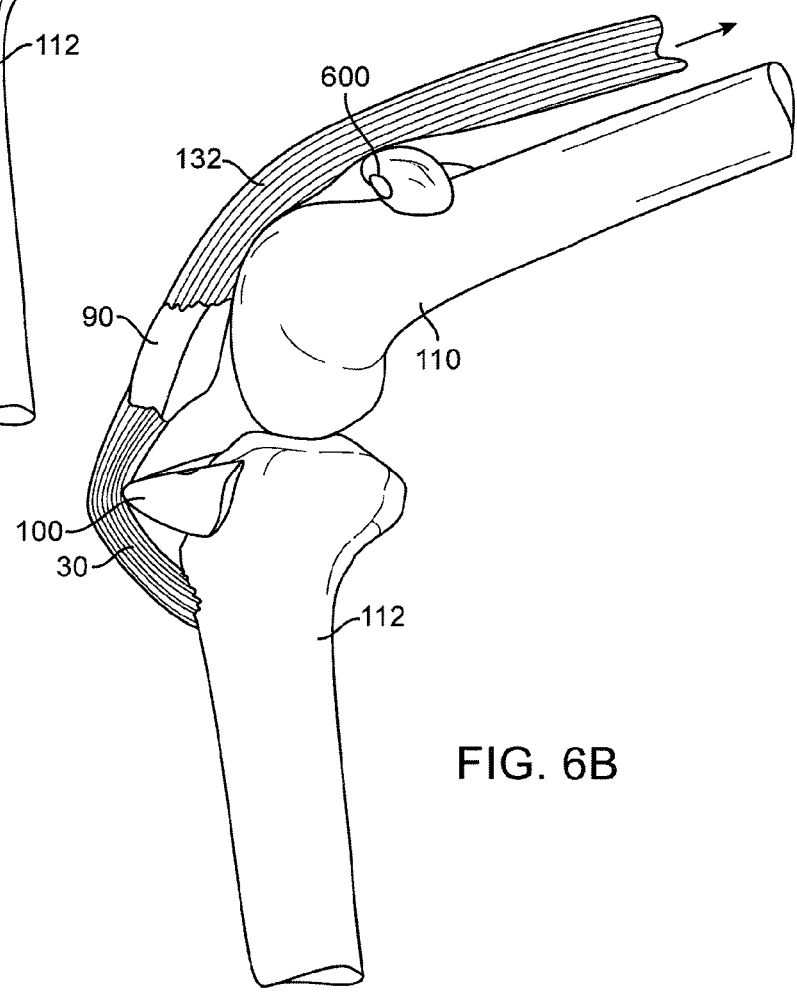

FIGS. 6A and 6B illustrate the reduction in load between the patella 90 and the femur 110 at about 75 degrees of flexion of the joint. As can be seen in FIG. 6B, the proximal portion of the patella 90 is lifted away from the femur 110, however the amount of load reduction my be tailored to the particular application by altering the configuration of the implants.

The patellar implants 100, 600 can be configured to include one or more structures that only applies tension during gait, and then, during only portions of the gait cycle. Such structure can also include a load absorption component acting during such intervals. Through this approach, undesirable permanent remodeling of knee structure, and in particular unwanted lengthening of the patellar tendon, can be avoided. One way to achieve intermittent activation of the implant is to have a multi-compartment expandable implant which inflates and deflates based on joint action. These inflatable implants will be described in further detail below.

Figure 7A:
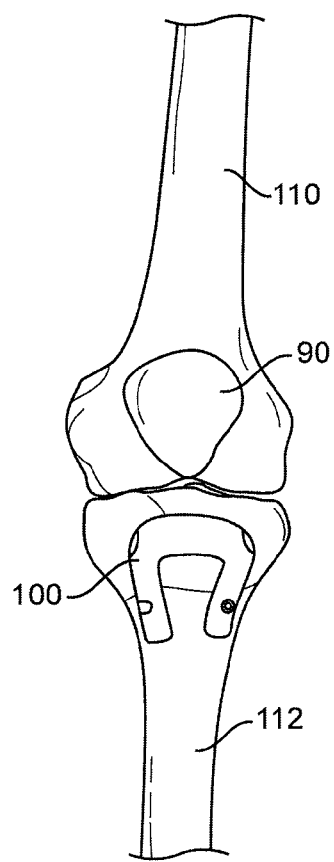
FIGS. 7A, 7B and 7C are front views, depicting implants attached to members of a joint with a tibial implant only, a femoral implant only and both tibial and femoral implants according to an alternative example embodiments of the present disclosure.
Figure 7B:
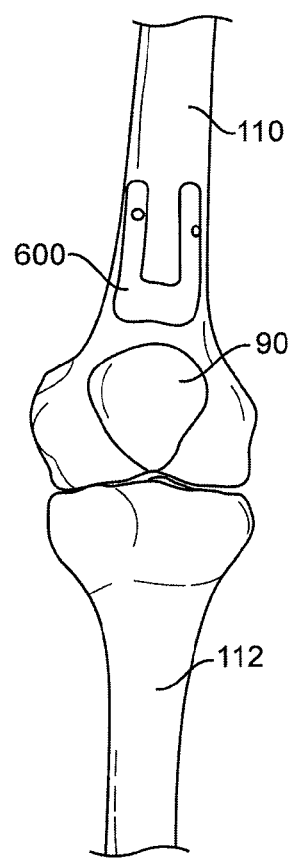
Figure 7C:
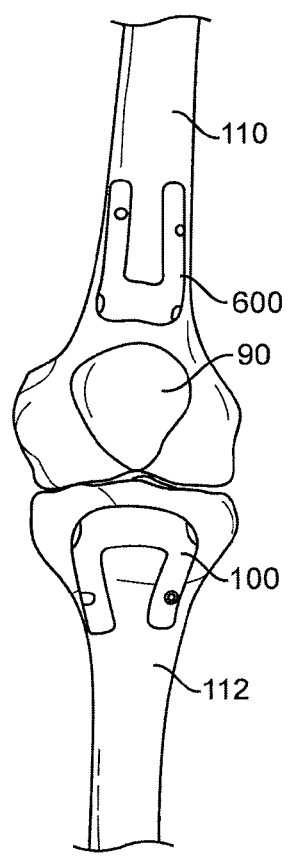

Referring now to FIGS. 7A-7C, the tibial implant 100 and femoral implant 600 can be used either alone or in combination. The implants of FIGS. 7A-7C have a C-shaped design that wraps around the bone shaft between 45 and 180 degrees of the circumference of the bone. The wrapping around of the C-shaped design allows several muscles and/or tendons to be redirected or repositioned by the implant.

FIG. 8A illustrates an I-shaped implant 610 configured to be attached to the femur 110. At the position shown in FIG. 8A the implant 610 would reside partly beneath the patella (not shown) when the knee joint is at full extension. The I-shaped implant sits at the end of the femur 110 near the joint and elevates the quadriceps muscle and tendon.

FIGS. 8B and 8C illustrate two variations of an I-shaped implant for the tibia. The wider implant 160 extends beyond the bone contact region and the narrower implant 170 does not extend past this contact region. These implants are shown in further detail in FIGS. 12A and 12B. FIGS. 8D and 8E illustrate J-shaped implants 180, 190 which have a single leg extending along the bone shaft for improved bone attachment. These different designs with different attachment mechanisms can provide the surgeon with options for attachment to bone with bone screw locations that avoid disruption to the ligaments, muscles and subchondral regions of the bone.

FIGS. 9A-9D illustrate different cross section profiles for the implants including those having top surfaces which are flat, saddle shaped, convex, or concave. These profiles can apply to both tibial implants 100 and femoral implants 600. The implant of FIG. 9A has a concave lower surface 650 configured to correspond generally to the shape of the bone and a convex upper surface 652 configured to support the overlying tendon or muscles. Medial and lateral flanges 654 at the edges of the top surface help prevent the tendons or muscles from sliding off of the implant. A plurality of feet 656 on the lower surface 650 are configured to contact the bone and allow for the implant to accommodate different anatomical variations between patients. At least one foot 656 and preferably three feet extend from the implant on the bone-facing surface or bottom surface of the implant to make contact with the bone. The feet provide an offset which allows the implant to be seated on the bone surface despite slight variations in bone surface geometries between patients and despite slight variations in positioning of the implant. The feet 656 can be provided on any of the embodiments of the implants described herein and will tightly contact the bone or the periosteum when the bone screws are tightened to press the implant against the bone.

FIG. 9B has a concave lower surface 660 and a substantially flat upper surface 662 with lateral flanges 664. Each of the implants has two or more holes for receiving bone screws. FIGS. 9C and 9D have various saddle shaped lower and upper surfaces with bone screws inserted from the proximal or distal side of the implant (FIG. 9C) and from the medial and lateral sides of the implant (FIG. 9D). The saddle top provides a stabilizing effect to keep the tendons or muscles from sliding off of the top of the implant.

Figure 10C:
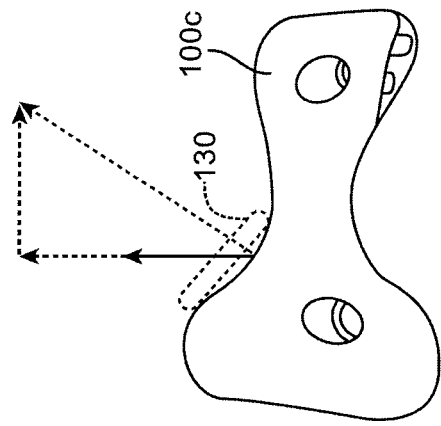
FIGS. 10A-10C are top views of implants having different inclinations of the superior surface according to alternative embodiments of the present disclosure.
Figure 10B:
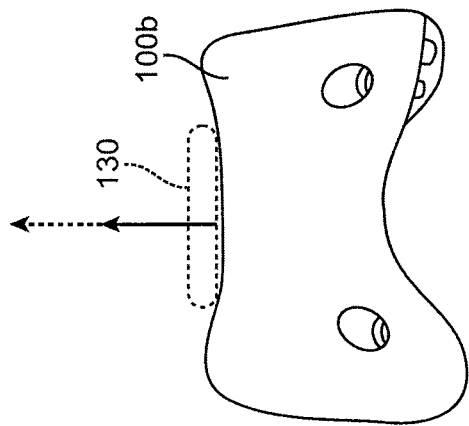
Figure 10A:
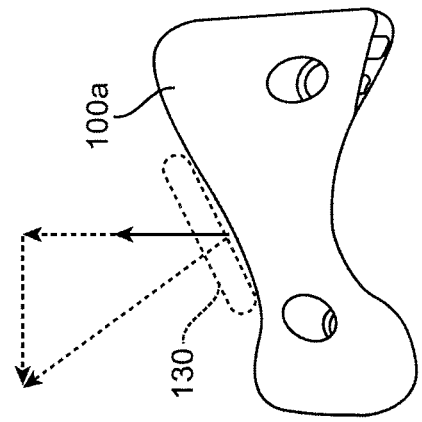

The flat top cross section of the implant 100b of FIG. 10B produces a one directional displacement of a tendon or muscle providing primarily unloading of the patella/femoral joint. The implant may also have an medial/lateral inclination as shown in the implant 100a of FIG. 10A to both reduce the load on the joint and also to shift the load on the joint medially or laterally. The implant 100c of FIG. 10C has a partly flat and partly angled surface which may both shift the load and reduce the load.

Figure 11C:
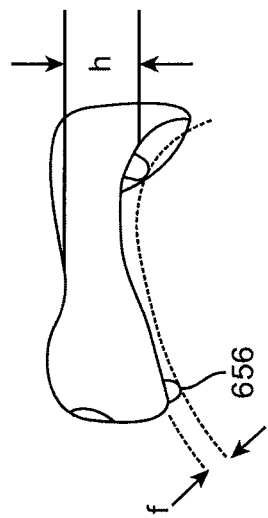
FIGS. 11A-11C are top views of implants having different heights and different shapes according to alternative embodiments of the present disclosure.
Figure 11B:
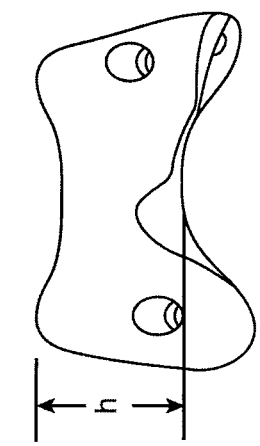
Figure 11A:
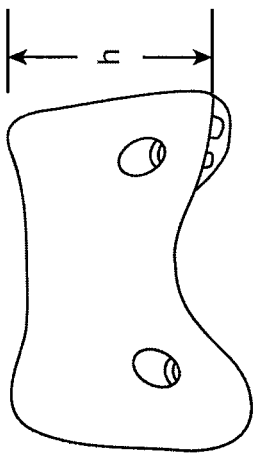

FIGS. 11A-11C show a series of implants of differing heights h. Implants having heights from 2 mm to 60 mm may be provided to allow the surgeon to select the implant that unloads the joint to the desired degree. FIG. 11C illustrates an offset height f provided by the feet 656. The height f of the feet is about 2-5 mm, preferably about 3 mm.

Figure 12A:
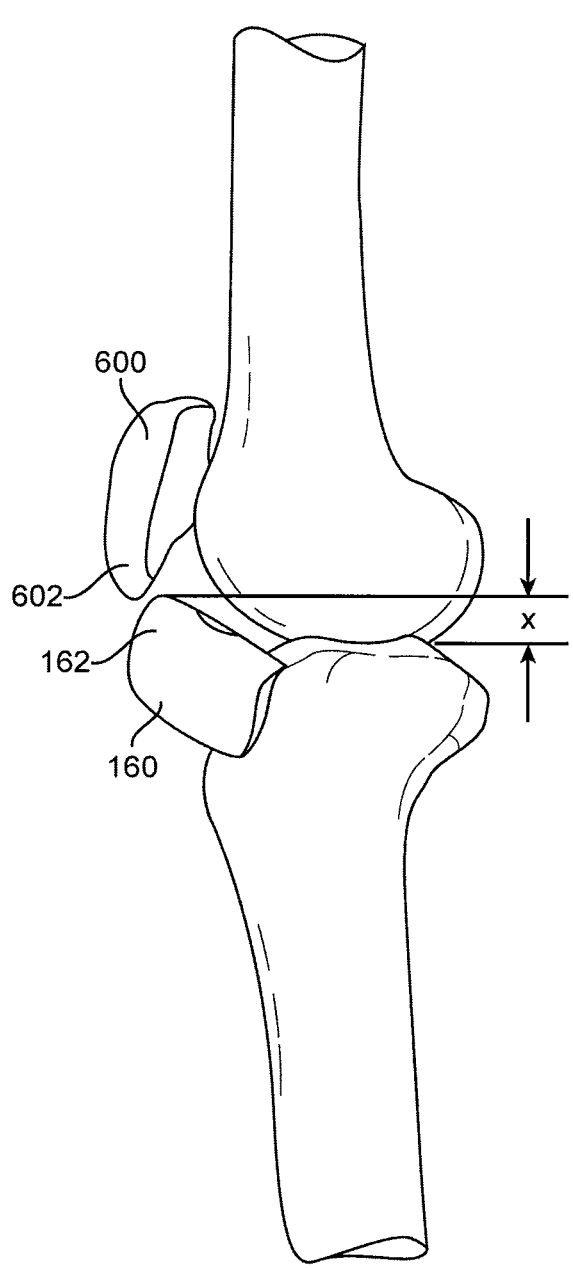
FIGS. 12A and 12B are side views, depicting the knee joint and implants having different extensions with respect to the joint surfaces of FIGS. 8B and 8C.
Figure 12B:
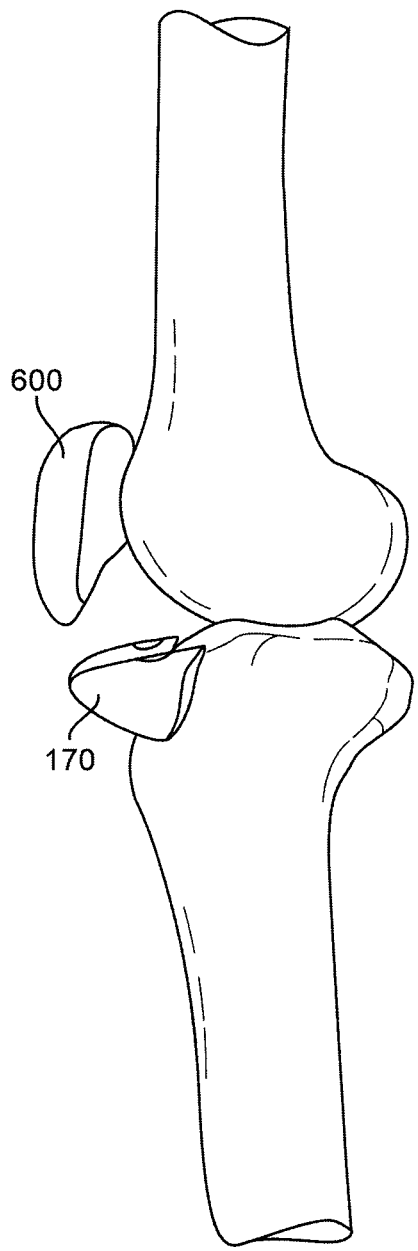

FIG. 12A further illustrates the tibial implant 160 which has an overhang or projection 162 which extends by a distance X beyond a line formed at the bone contacting surfaces. This overhang 162 increases the effectiveness of the implant 160 at larger angles of flexion. The femoral implant 600 is also provided with an overhang 602, however the overhang of the femoral implant does not extend beyond the joint contact surfaces. The implant 170 of FIG. 12B shows no overhang, however the implant is positioned close to or adjacent the joint contact surfaces.

Figure 13:
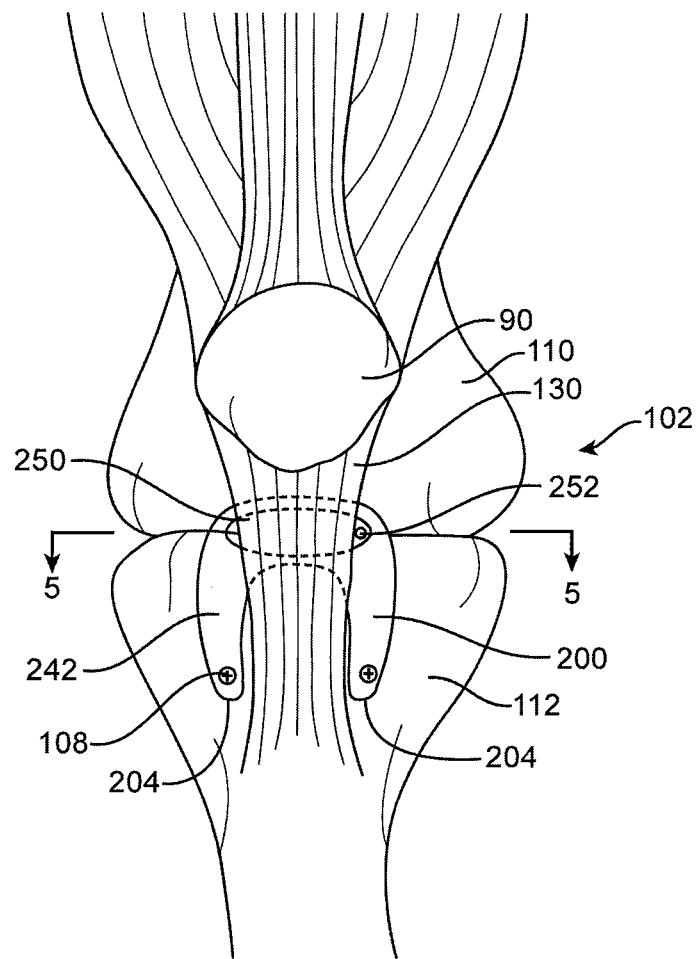
FIG. 13 is a front view, depicting an implant attached to members defining a joint according to alternative example embodiment of the present disclosure.
Figure 14:
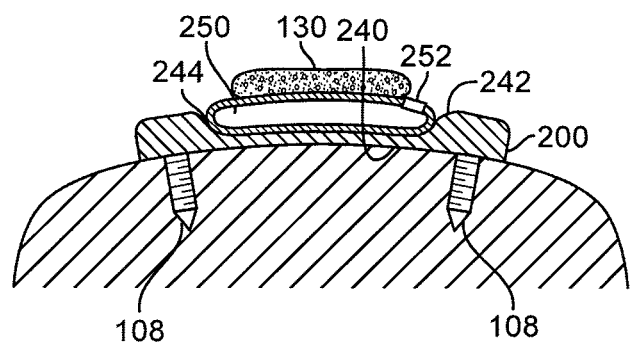
FIG. 14 is a cross-sectional view, depicting the structure of FIG. 1 taken along lines 5-5.

Referring to FIGS. 13 and 14, there is shown another embodiment of an implant 200. As before, the implant can be generally U-shaped, C-shaped, I-shaped or J-shaped and includes terminal ends 204 configured to be affixed to body anatomy. Again, through holes are provided to receive affixation structure such as bone screws 108 so that the implant can be attached directly to knee anatomy. A lower surface 240 of the implant 200 be curved to mimic the shape of the structure to which the implant 200 engages, such as the tibia 112 or femur 110. An upper surface 242 of the implant 200 is intended to be lubricous to permit relative movement with a patellar tendon 130. Moreover, the implant 200 can be configured with its terminal ends 204 directed toward or away from the knee joint 102 and can include a midsection with a recess 244 shaped to receive the patellar tendon 130 through a full range of motion of the knee.

This embodiment of the implant further includes a fluid, gas or gel filled chamber or bladder 250 which is accessible by an injection port 252. The chamber 250 can form an integral structure with remaining portions of the implant 200 and portions of the implant 200 can embody fiber woven reinforced fixation material to form a single bodied structure. The injection port 252 is employed to both place substances within the chamber 200 and to be accessible to alter the volume or composition of the substance before and after implantation. The injection port 252 can also be used to remove all or most fluid when implanting or removing the implant 200 or to alter the softness or rigidity of the implant. The structure defining the chamber 250 can have an elasticity greater than that chosen for the remaining portions of the implant 200, such as for example the terminal ends 204 which are designed to have a rigidity or robustness suited for permanent attachment to knee anatomy. The materials are of course chosen to be biocompatible in any event.

The substance chosen to fill the chamber 250 is selected to cooperate with the material chosen for walls defining the chamber 250 so that desired load redirection can be effectuated. It is further contemplated to take advantage of fluid responses of the substances chosen for placement within the chamber 250. For example, a viscous fluid or gel such as silicone hydrogel flows smoothly under low strain rates, but resists flow under high strain rates. Therefore, the fluid or gas chosen is intended to have a viscosity and the chamber walls are designed to have a flexibility to redirect load to alleviate pain. Such load redirection can be reserved to occur primarily gait, and for that matter, during only portions of gait with greater flexion angles. During joint extension, or otherwise when there is less pain due to forces associated with the patella this manipulation is reduced so that undesirable remodeling is avoided.

Thus, as the knee joint 102 articulates during gait, the patellar tendon 130 is guided through the implant recess 244. The load redirecting chamber 250 is sized and shaped to span the recess 244 so that during certain portions of gait having medium to high flexion angles, a height of the chamber 250 is at a maximum to provide maximum load redirection and reduced load applied directly between the patella 90 and femur 110. For example, forces between the patella 90 and the femur 110 can be reduced and angles of action of the patellar tendon 130 can be modified to thereby minimize pain.

Figure 15:
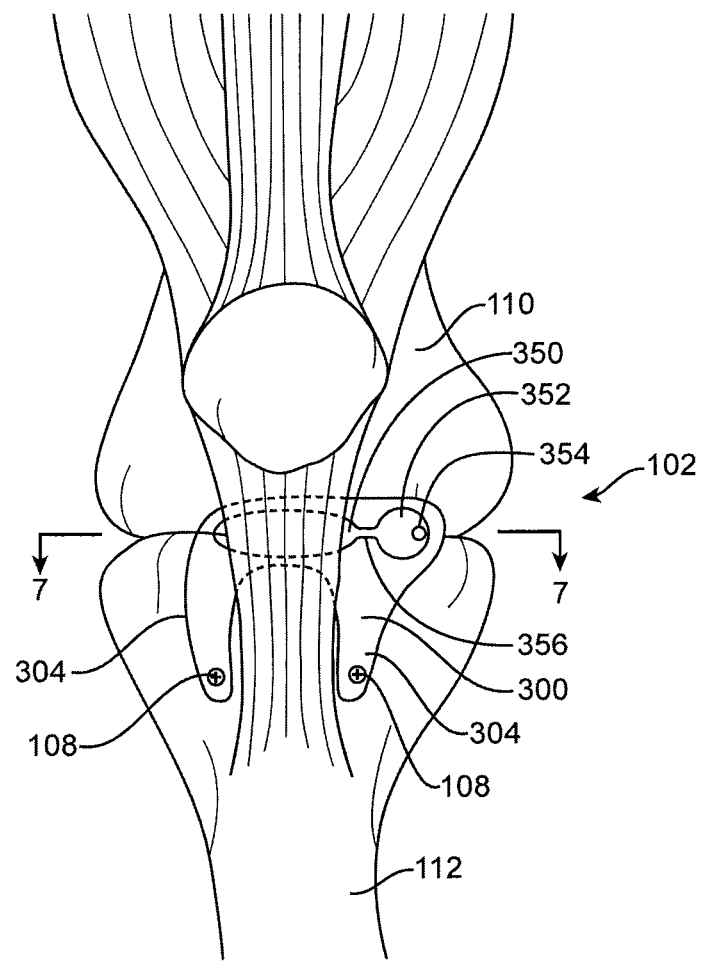
FIG. 15 is yet another front view, depicting an implant attached to members defining a joint according to alternative embodiments of the present disclosure.
Figure 16:
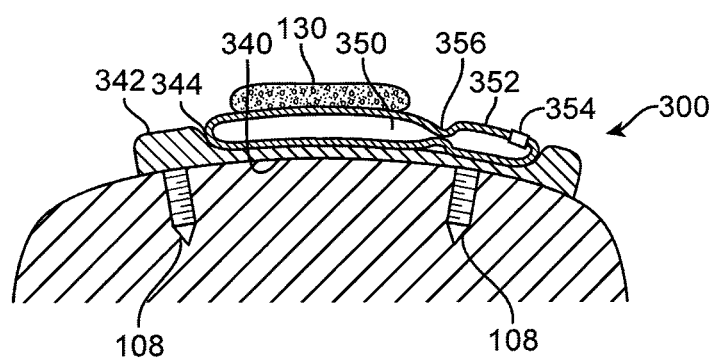
FIG. 16 is a cross-sectional view, depicting the structure of FIG. 1 taken along lines 7-7.
Figure 17:
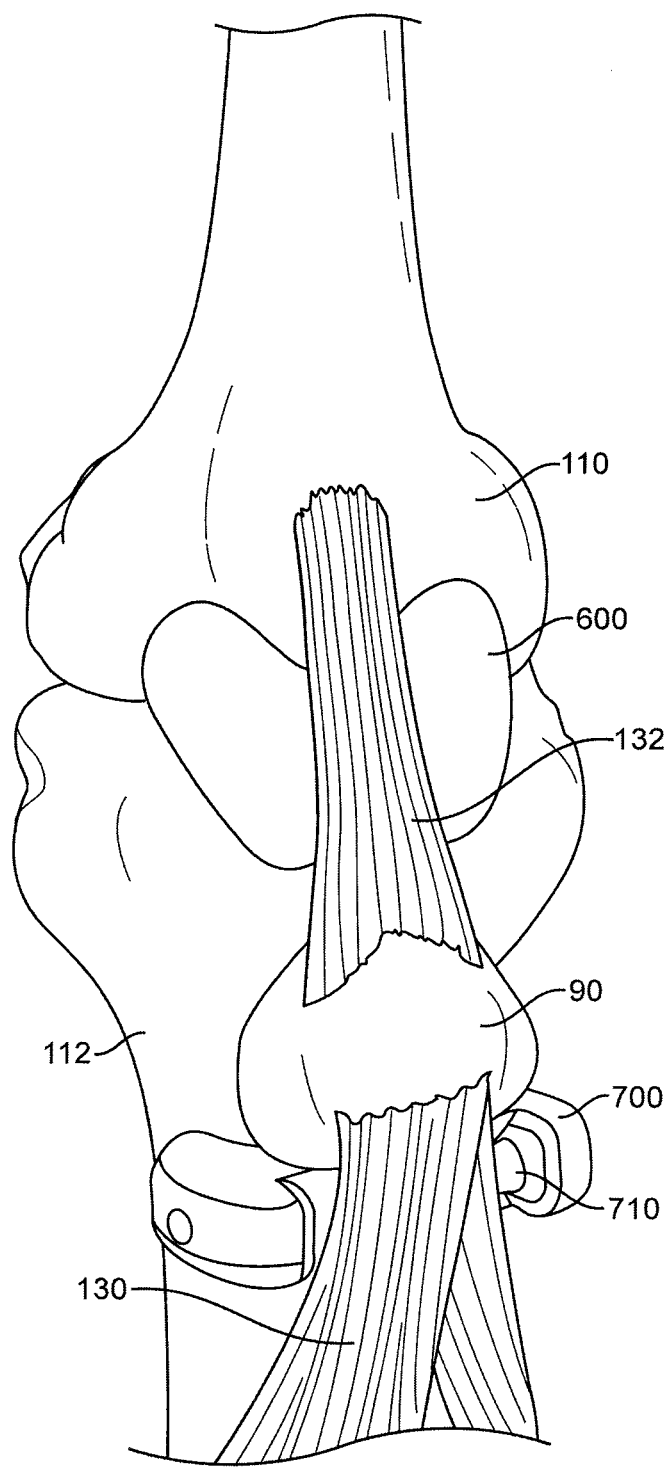
FIG. 17 is a front perspective view depicting an implant with a roller according to an alternative embodiment of the present disclosure.

In yet another approach (FIGS. 15 and 16), the implant 300 can further include multiple chambers 350, 352 that are in fluid communication and which are versatile in accommodating tension and contact forces. As before, a lower surface 340 of the implant 300 be curved to mimic the shape of the structure to which the implant 300 engages, such as the tibia 112 or femur 110. An upper surface 342 of the implant 300 is intended to be lubricous to permit relative movement with a patellar tendon 130. Moreover, the implant 300 can be configured with its terminal ends 304 directed toward or away from the knee joint 102 and can include a midsection with a recess 344 shaped to receive the patellar tendon 130 through a full range of motion of the knee.

The generally U-shaped device can be extended to provide a platform about each of the chambers 350, 352. Here, again, the chambers 350, 352 are designed to receive gases or fluids which embody desirable viscosity characteristics. Additionally, the first chamber 350 is intended to be arranged to be in apposition with the patella tendon 130 and the second chamber 352 is to be positioned remote from the tendon 130 in an area where the chamber will be free to fill and empty in a relatively unobstructed manner. Also, as before, the walls defining the chambers 350, 352 are formed from materials having an elasticity designed to achieve desired force reorientation throughout the full range of motion of the knee joint. An injection port 354 is additionally included to provide access to the second chamber 352 so that the volume or composition of the substance in the chamber can be altered.

A neck 356 joining the first 350 and second 352 chambers provides the fluid communication between the structures. A valve (not shown) can be configured in this area or the neck 356 can define a small opening. In either approach, the neck 356 can be configured to play a role in the movement of fluid from one chamber to the next. For example, when a leg of an individual is in extension, there is no force or little force on the first chamber 350. The elasticity of the second chamber 352 is chosen to thus cause fluid to flow into the first chamber 350. During gait, the sizing of the neck 356 is such that its flow access is limited so that there is insufficient time for fluid to pass from the first chamber 350 to the second chamber 352. Rather, the fluid remains but flows within the first chamber 350 to thereby provide force reorientation. When seated or otherwise placing the knee joint 102 in other resting or non-gait positions, with the joint in flexion, the force of the patellar tendon 130 presses fluid out of the first chamber 350 into the second chamber 352. As such, the first chamber 350 is reduced in size during this juncture, and the patellar tendon 130 is not subjected to the increased tension caused by the implant 300. By not engaging in this manipulation, the patellar tendon 130 can be unloaded and remodeling thereof is avoided.

In another embodiment, the second chamber 352 can be positioned within an anatomical structure, such as a muscle, and the fluid will be forced into the first chamber 350 by activation of the muscle. Therefore, the implant 300 can be activated by muscle activation, such as during running or walking, and can remain relatively passive at other times.

FIGS. 17-20 illustrate a further embodiment of an implant 700 having a roller 710. The implant 700 is designed to further reduce the friction between the implant and the tissue sliding over it. The roller 710 makes contact with the tendons, muscles and other tissues to reduce potential tissue irritation including tendonitis, inflammation, tendon tears and rupture. The roller 710 is supported in the implant 700 within blind bores 712 by bearing rollers 714. Bearing rollers 714 are protected by a seal 716 in the form of O-rings, quad rings, lip seals or the like.

Figure 21:
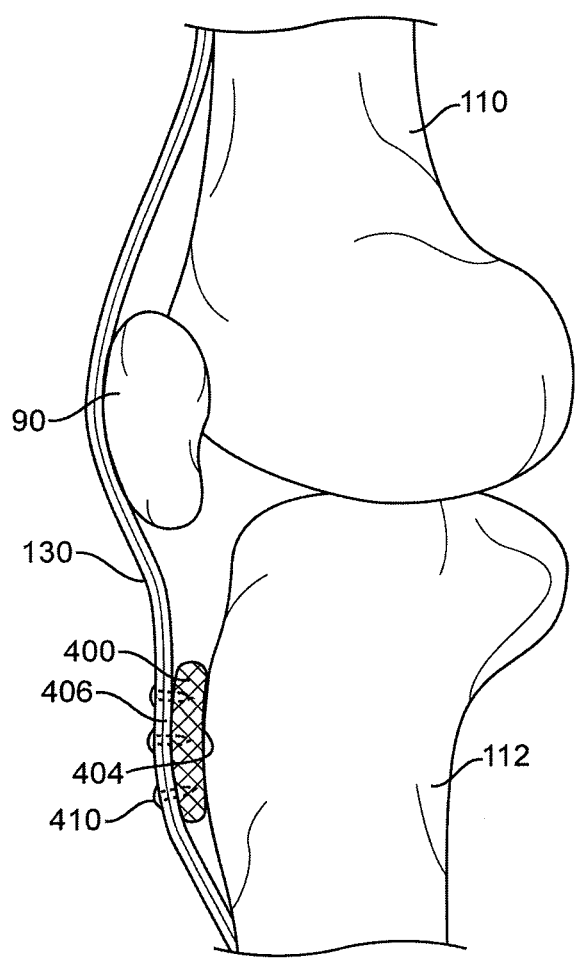
FIG. 21 is a side view, depicting an implant according to alternative embodiments of the present disclosure.
Figure 22:
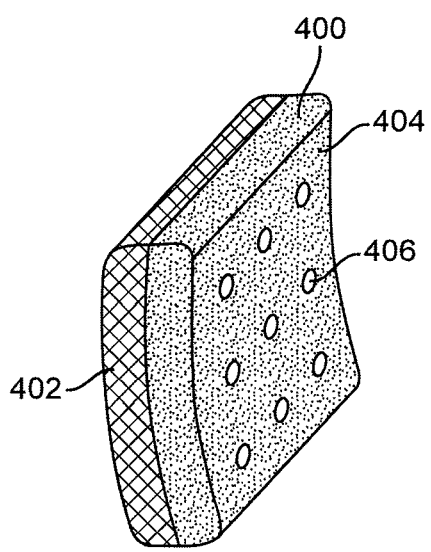
FIGS. 22 and 23 are perspective views, depicting the implant of FIG. 21.
Figure 23:
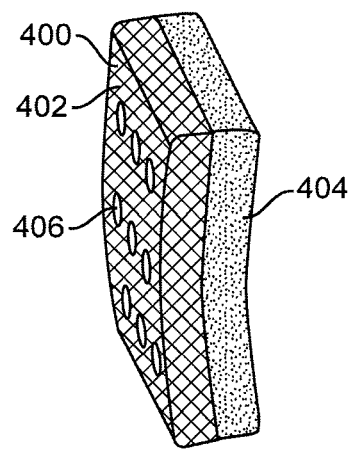

In a related approach, as shown in FIGS. 21-23, an implant 400 designed to accomplish force reorientation can be affixed directly to the patellar tendon 130. This implant 400 can further include one or more of the features described above including one or more fluid filled chambers. Further, it is again contemplated that the device be formed from biocompatible materials. This particular implant 400 further embodies a porous or mesh tendon contacting surface 402 and a lubricious bearing surface 404 for sliding contact with bone. The porous mesh surface 402 supports ligament ingrowth and aids in attachment to the patellar tendon 130. The lubricious bearing surface 404 slides along knee anatomy during articulation. Through holes 406 are further provided and sized and shaped to receive fastening structures 410 for assuring a strong affixation to the patellar tendon 130. In this way, relative movement between the implant 400 and ligament is eliminated and the implant 400 is thus always correctly positioned to provide desired force reorientation and pain relief. Other methods for attachment of the implant 400 to the patellar tendon 130 or other tendons or muscles may also be used including known tissue ingrowth surfaces on the implant, sutures, mechanical clamping or combinations of attachment mechanisms. There is no risk of the patellar tendon remodeling around the implant 400 because the implant is connected directly to the tendon.

Figure 24:
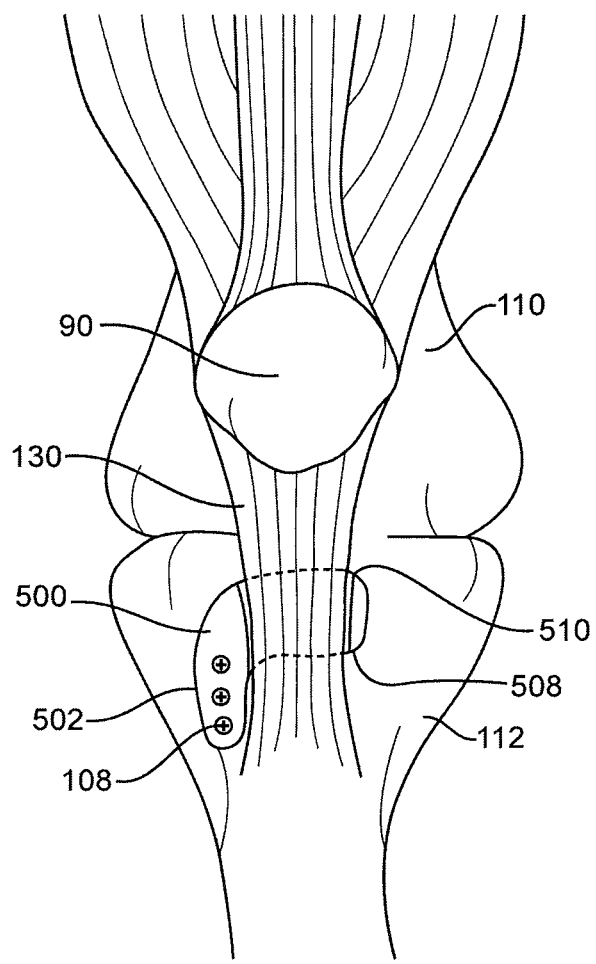
FIG. 24 is a front view, depicting an implant placed at a joint according to an alternative embodiment of the present disclosure.

With reference to FIG. 24, there is shown in yet another embodiment of an implant 500. This implant 500 can include one or more of the above described features, such as one or more chambers, and further embodies a generally inverted J-shape. A vertically extending portion 502 of the implant 500 is provided with through holes sized and shaped to receive fastening structure such as bone screws 108. A laterally extending portion 508 includes a recess 510 for receiving a patellar tendon 130. Although the implant 500 is shown attached to the tibia 112, it can also be affixed to the femur 110 as well. This approach illustrates that an asymmetric implant can be employed to accomplish desired treatment of the patella 90. A further deviation would be to eliminate the vertically extending portion 502 and to include affixation structure within the recess 510. The implant 500 also has a trough or recess as in the implant shown in FIG. 2 to guide in tracking the patellar tendon over the implant in a desired trajectory.

Figure 25:
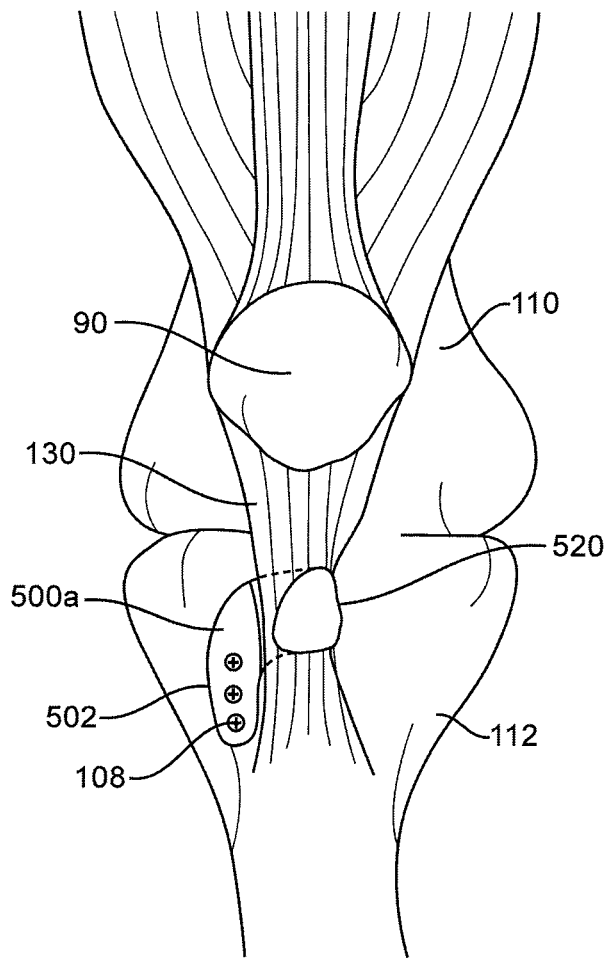
FIG. 25 is a front view, depicting a an implant placed at a joint according to an alternative embodiment of the present disclosure.

FIG. 25 shows a hook shaped implant 500*a* which functions to both elevate the tendon 130 and to alter the tracking of the patella 90. A hook 520 can move the patellar tendon and consequently the patella itself laterally, such as toward the lateral side of the knee when the patella pain is caused by improperly tracking to far to the medial side. The hook 520 is sized to receive at least a portion the tendon underneath the hooked portion of the implant.

Figure 26:
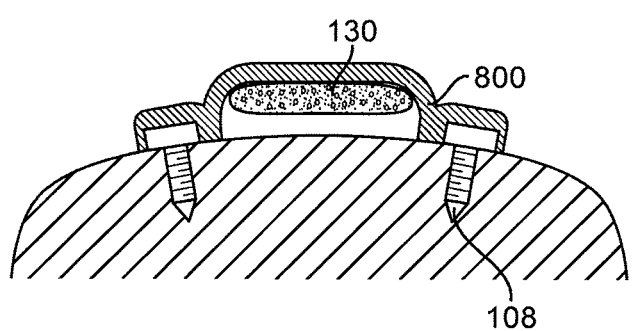
FIG. 26 is a cross-sectional view of an implant according to an alternative embodiment of the present disclosure.

FIG. 26 illustrates a bridge shaped implant 800 which lifts the patellar tendon 130 in a manner similar to the lift implants shown herein, but lifts from the superior surface of the patellar tendon rather than from the inferior surface. The bridge can be attached to the patellar tendon 130 by sutures, mechanically clamped, tissue ingrowth or a combination thereof.

The various embodiments of the implants describe herein may be made from a wide range of materials. According to one embodiment, the implants are made from metals, metal alloys, or ceramics such as, but not limited to, Titanium, stainless steel, Cobalt Chrome or combinations thereof. Alternatively, the implants are made from thermo-plastic materials such as, but not limited to, high performance polyketones including polyetheretherketone (PEEK), ultra-high molecular weight polyethylene (UHMWPE), PyroCarbon or a combination of thermo-plastic and other materials. Various embodiments of the implants are relatively rigid structures.

Conventional approaches to inserting the above-described implants within knee anatomy are contemplated. Arthroscopic approaches can be employed along with fluoroscopy or other imaging techniques to properly position the treatment devices. Prior to implantation, the anatomy of the patient's knee is accessed to determine a best course of treatment, and to identify a configuration of implant which best suits the patient's specific condition. The knee is rotated and turned through its full range of motion to identify proper implantation sites and to access the best manner for redistributing tensions and contact forces, with the objective of reducing pain. Further, the implant is configured in its most compressed configuration for implantation and then reconfigured to function in a treatment capacity. Subsequent to implantation, the implant can be reconfigured to present an altered profile to achieve optimum results.

The foregoing therefore provides an implant embodying a compliant bolster and lengthening affect to increase a moment arm of the bolstered patellar tendon for the purpose of relieving pain or other symptoms involving the patella. The size or stiffness of the implant can be altered to achieve the desired bolstering or manipulation of tension and contact forces.

Thus, it will be apparent from the foregoing that, while particular forms of the apparatus and method have been illustrated and described, various modifications can be made without parting from the spirit and scope of the disclosure. In particular, one or more features of one specific approach can be incorporated into another approach. Additionally, the present disclosure can be made to be applicable to other medical conditions.

We claim:

1. A knee joint implant, comprising:
   a patellar tendon engaging portion, the patellar tendon engaging portion configured to engage a patellar tendon throughout a full range of motion of a knee joint; and
   a tension redistribution and contact force manipulation portion configured to alleviate pain associated with patella misalignment;
   wherein the patellar tendon engaging portion comprises a first chamber containing a fluid and a second chamber in fluid communication with the first chamber.

2. The knee joint implant of claim 1, wherein the tension redistribution and contact force manipulation portion is configured to operate during less than an entire portion of a gait cycle.

3. The knee joint implant of claim 1, wherein the first chamber contains a hydrogel.

4. The knee joint implant of claim 1, further comprising a neck structure joining the first chamber and the second chamber.

5. The knee joint implant of claim 4, further comprising a valve within the neck structure.

6. The knee joint implant of claim 4, wherein the neck structure is configured to control movement of said fluid between the first chamber and the second chamber.

7. The knee joint implant of claim 1, further comprising an injection port through which the fluid can be passed into or out of the first chamber.

8. The knee joint implant of claim 1, further comprising an injection port through which the fluid can be passed into or out of the first chamber or the second chamber.

9. The knee joint implant of claim 1, wherein the fluid flows within the first chamber to provide a range of tension redistribution and contact force manipulation during portions of a gait.

10. The knee joint implant of claim 1, wherein the fluid flows between the first chamber and the second chamber to provide a range of tension redistribution and contact force manipulation during portions of a gait.

11. The knee joint implant of claim 1, wherein the fluid passes to the second chamber during rest and when the patellar tendon is straightened to relieve tension on the patellar tendon and to avoid remodeling of anatomy.

12. The knee joint implant of claim 1, wherein the implant is configured to avoid permanent remodeling of knee anatomy.

13. The knee joint implant of claim 1, wherein the fluid comprises a substance which exhibits a smooth flow of the substance under low strain rates, and which resists flow under high strain rates.

14. The knee joint implant of claim 1, wherein the implant defines a bolster and creates a patellar tendon lengthening effect to increase a moment arm of a bolstered patella tendon when positioned below a patella tendon.

15. The knee joint implant of claim 1, further comprising at least one fastener configured to attach the implant to knee anatomy.

16. The knee joint implant of claim 15, wherein the implant is configured so that, when the implant is attached to the patellar tendon, relative motion between the implant and the patellar tendon is eliminated.

17. The knee joint implant of claim 16, the patellar tendon engaging portion further comprises an upper side configured to face the patellar tendon, the upper side including a tissue ingrowth structure.

18. The knee joint implant of claim 17, the patellar tendon engaging portion further comprising a lower side including a lubricious surface.

* * * * *